United States Patent
Schaefers

(10) Patent No.: US 10,802,092 B2
(45) Date of Patent: Oct. 13, 2020

(54) DEVICE AND METHOD FOR TESTING THE MR-SAFETY OF IMPLANTS

(71) Applicant: MR COMP GmbH, Gelsenkirchen (DE)

(72) Inventor: Gregor Schaefers, Bottrop (DE)

(73) Assignee: MR COMP GmbH, Gelsenkirchen (DE)

( * ) Notice: Subject to any disclaimer, the term of this patent is extended or adjusted under 35 U.S.C. 154(b) by 0 days.

(21) Appl. No.: 16/326,198

(22) PCT Filed: Aug. 16, 2017

(86) PCT No.: PCT/EP2017/070790
§ 371 (c)(1),
(2) Date: Feb. 17, 2019

(87) PCT Pub. No.: WO2018/033583
PCT Pub. Date: Feb. 22, 2018

(65) Prior Publication Data
US 2019/0187226 A1 Jun. 20, 2019

(30) Foreign Application Priority Data

Aug. 16, 2016 (DE) .......... 10 2016 115 216

(51) Int. Cl.
*G01V 3/00* (2006.01)
*G01R 33/28* (2006.01)
*A61N 1/08* (2006.01)

(52) U.S. Cl.
CPC ............ *G01R 33/288* (2013.01); *A61N 1/08* (2013.01)

(58) Field of Classification Search
USPC .......................................... 324/307
See application file for complete search history.

(56) References Cited

U.S. PATENT DOCUMENTS

| | | | | |
|---|---|---|---|---|
| 2008/0297151 | A1* | 12/2008 | Hirata ..................... | G01R 33/58 324/307 |
| 2010/0253338 | A1* | 10/2010 | Eryaman .............. | G01R 33/285 324/309 |
| 2011/0066028 | A1 | 3/2011 | Min et al. | |
| 2012/0086449 | A1* | 4/2012 | Graesslin ............. | G01R 33/285 324/309 |
| 2013/0102880 | A1* | 4/2013 | Gulsen ............... | G01R 33/4804 600/412 |
| 2014/0009154 | A1* | 1/2014 | Hausotte Geb Bakai ................... | G01R 33/58 324/309 |

(Continued)

OTHER PUBLICATIONS

International Search Report and Written Opinion dated Dec. 18, 2017 from the International Searching Authority Re. Application No. PCT/EP2017/070790 and its Translation into English. (12 pages).

(Continued)

*Primary Examiner* — Rodney E Fuller

(57) ABSTRACT

A device and a method for testing the MR-safety of an implant (4). The device includes a phantom (1) that has a test volume filled with a medium (2), wherein the test volume receives the implant (4) to be tested, at least one RF transmitter (3) that emits radio-frequency electromagnetic radiation into the test volume. The device is used for detecting the heating of the implant (4) and/or of the medium (2) surrounding the implant.

12 Claims, 1 Drawing Sheet

(56) References Cited

U.S. PATENT DOCUMENTS

| | | | | |
|---|---|---|---|---|
| 2014/0191754 | A1* | 7/2014 | Ringholz | G01R 33/20 |
| | | | | 324/315 |
| 2014/0249612 | A1* | 9/2014 | Bonmassar | C09K 19/3809 |
| | | | | 607/116 |
| 2015/0297316 | A1* | 10/2015 | Grinstaff | A61B 90/39 |
| | | | | 600/414 |
| 2016/0306021 | A1* | 10/2016 | Weber | A61N 1/403 |
| 2016/0331960 | A1* | 11/2016 | Katnani | A61N 1/086 |
| 2017/0205477 | A1* | 7/2017 | Grodzki | G01R 33/288 |
| 2017/0336490 | A1* | 11/2017 | Suh | A61B 6/032 |
| 2018/0011158 | A1* | 1/2018 | Katscher | A61B 5/055 |
| 2018/0130381 | A1* | 5/2018 | Tian | B29C 39/10 |
| 2019/0383895 | A1* | 12/2019 | Zuccolotto | G01R 33/58 |

OTHER PUBLICATIONS

Elster LLC "Birdcage Coils", Birdcage RF Coil—Questions and Answers, Elster LLC, 2 P., Nov. 2016.

Oh et al. "Experimental and Numerical Assessment of MRI-Induced Temperature Change and SAR Distributions in Phantoms and In Vivo", Magnetic Resonance in Medicine, 63(1): 218-223, Jan. 2010.

* cited by examiner

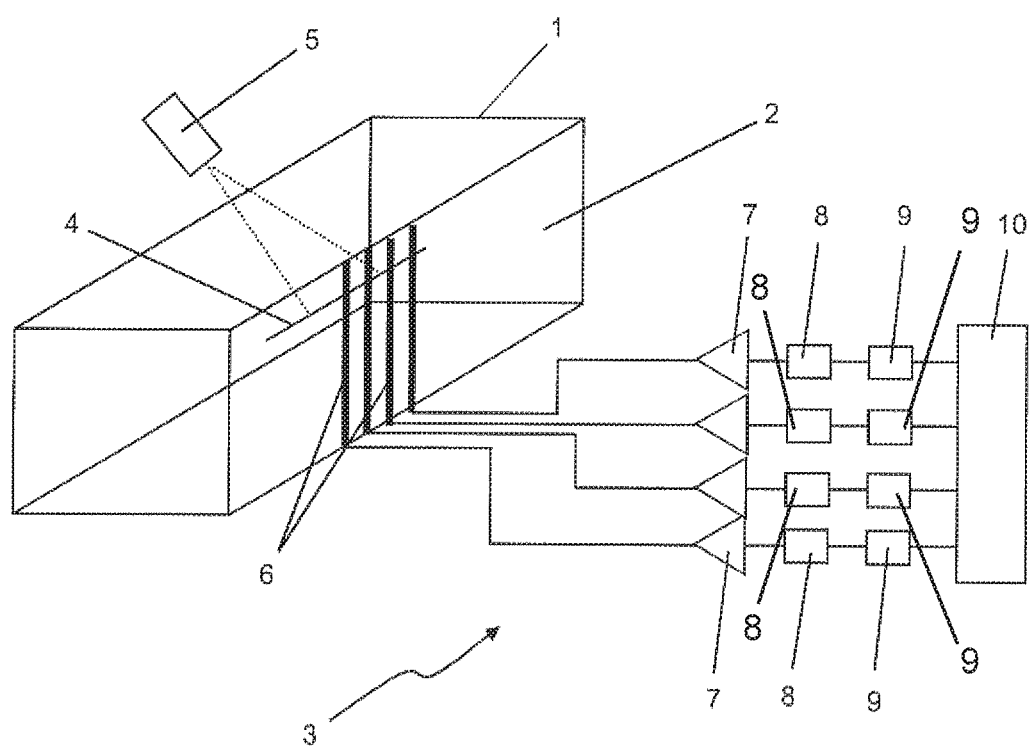

DEVICE AND METHOD FOR TESTING THE MR-SAFETY OF IMPLANTS

RELATED APPLICATIONS

This application is a National Phase of PCT Patent Application No. PCT/EP2017/070790 having International filing date of Aug. 16, 2017, which claims the benefit of priority of German Patent Application No. 10 2016 115 216.1 filed on Aug. 16, 2016. The contents of the above applications are all incorporated by reference as if fully set forth herein in their entirety.

FIELD AND BACKGROUND OF THE INVENTION

Imaging medical diagnosis by means of magnetic resonance (MR), also referred to as magnetic resonance tomography (MRT) or magnetic resonance imaging (MRI), is widespread. In order to generate measurable MR signals, the body of the patient to be examined is subjected to high-power (several 100 W to several kW) radio-frequency (RF) electromagnetic radiation (at frequencies in the range between 5 MHz and several 100 MHz), in the MR systems used. Some of the RF radiation is absorbed in the body tissue and causes heating there during the MR examination. In particular, the RF radiation is absorbed in medical implants that are located in the body and contain metal. Said implants heat up particularly significantly and can therefore lead to injury in the surrounding tissue and thus constitute a safety risk.

It is therefore important to ascertain the safety of a particular implant for MR examinations (MR-safety) in advance, i.e. before a patient who has an implant of this kind undergoes an MR examination.

In vivo measurement of the heating of the implant or the tissue surrounding said implant, or the RF absorption in/at the implant, which absorption leads to corresponding heating, is difficult.

There is therefore a need for devices and methods which allow for a risk-free and reliable test of the MR-safety of an implant outside the body.

SUMMARY OF THE INVENTION

For this purpose, the invention proposes a device for testing the MR-safety of an implant, comprising a phantom that has a test volume filled with a medium, wherein the test volume receives the implant to be tested, at least one RF transmitter that emits radio-frequency electromagnetic radiation into the test volume, and comprising means for detecting the heating of the implant and/or of the medium surrounding said implant. These also include means for detecting electromagnetic measured variables (e.g. absorbed radiant power) which allow for conclusions to be drawn regarding the heating.

The medium of the test volume may be a liquid, a gel, air, or a mixture of these materials.

According to the invention, the implant to be tested is therefore introduced into the test volume of the phantom and exposed to RF radiation therein, wherein the situation in an MR examination is reproduced. In the process, the heating of the implant or of the medium surrounding said implant is measured, e.g. by means of temperature sensors, which are likewise located in the test volume, preferably in the medium and in the vicinity of the implant, or in a contactless manner, e.g. by means of suitable optical fiber thermometers or by means of other radiation thermometers. The heating can also be determined (indirectly) by means of sensors for detecting the electrical and/or magnetic field strength, or by means of other types of sensors.

The invention furthermore proposes a method for testing the MR-safety of an implant, wherein a test volume that is filled with a medium receives the implant to be tested and is subjected to radio-frequency electromagnetic radiation by means of at least one RF transmitter, wherein the heating of the implant and/or of the medium surrounding said implant is detected. This also covers the detection of the change in the electromagnetic fields in the presence of the implant, from which it is possible to draw conclusions regarding the heating.

In a preferred embodiment of the device according to the invention, the RF transmitter comprises an assembly of a plurality of antenna elements, wherein each antenna element can be supplied with an RF signal having an amplitude and/or phase that can be individually specified for said antenna element. The assembly of a plurality of antenna elements forms an antenna array, the individual elements of which are in each case selectively supplied with an RF signal having an individually adjustable amplitude and/or phase, in order for it to thus be possible to variably adjust virtually any RF field distribution in the test volume, in particular at the location of the implant to be tested. The aim in this case is to reproduce, as optimally as possible, the situation in a real MR examination. A further aim is to identify the virtual "worst-case" situation, i.e. the electromagnetic field distribution at which the RF absorption, and thus the heating, is at a maximum. Said worst case, i.e. the maximum possible heating of the implant, is the decisive criterion for assessing the implant as safe or unsafe for MR examinations. Against this background, the heating is expediently determined for different adjusted field distributions, and those field distributions at which the heating is maximum are used for determining the MR-safety. The implant is characterized as MR safe (or conditionally MR safe) if the maximum heating is below a specified threshold value.

For this purpose, the antenna elements are expediently connected to a multi-channel RF transmitter amplifier, wherein the amplitude and/or phase can be individually adjusted in each channel. The RF transmitter amplifier may for example consist of an RF synthesizer, the output signal of which is split over a plurality of channels. In this case, each channel contains a variable attenuator for adjusting the amplitude of the RF signal and a phase shifter for adjusting the phase of the RF signal in said channel. An RF amplifier is provided in each channel, in order to provide the RF power required for the relevant antenna element.

In a particularly preferred embodiment, the antenna elements are microstrips which extend in parallel with at least one surface of the test volume. Microstrips are dielectric waveguides which consist of one or more thin, conductive strips which are applied to a dielectric or extend in the vicinity of a dielectric. Microstrip lines may consist for example of narrow conductor strips that are arranged in a plane and are arranged in or above a metal surface, so as to be insulated. Microstrips make it possible to produce antenna structures of defined impedances, in a cost-effective and reproducible manner.

The antenna elements are preferably mutually parallel, straight microstrips. In this manner, an array of antennae can be formed (e.g. having a dipole-like characteristic in each case), by means of which almost any desired RF field distribution can be generated in the test volume by means of correspondingly specifying the amplitudes and phases of the RF signals. In this case, the microstrips may be directly applied to the surface of the test volume, or to a wall that defines the test volume. This renders the device according to the invention particularly simple and cost-effective, and lead to a high degree of reproducibility in the RF generation. Stable adaptation of the antenna elements can also be achieved in this manner. The electromagnetic radiation generated is coupled directly into the medium with which the test volume is filled, i.e. without losses at interfaces between different media.

It has been found to be expedient, in practice, to use a test volume having a cuboid geometry, wherein the microstrips of the antenna assembly extend substantially transversely to the direction of the longitudinal extension of the cuboid. This makes it possible to generate an electromagnetic field distribution inside the test volume in which the electrical field component extends substantially in parallel with the longitudinal extension of the test volume. The RF absorption in the implant is at a maximum when the direction of the electromagnetic field extends in parallel with the surface of the implant. In order to examine the maximum heating, in this embodiment the implant can accordingly simply be oriented so as to be in parallel with the longitudinal extension of the test volume. This is significant in particular in the case of elongate implants, for example in the case of wire-like implants, such as catheters or electrodes. In principle, the implant can be introduced into the test volume in any desired orientation, for example a wire-like implant along a specific trajectory or at particular angles.

In order to reproduce the real conditions in the body tissue, the electric permittivity and the electrical conductivity of the medium with which the test volume of the phantom is filled should correspond, as far as possible, to those of biological tissue. The thermal conductivity and the density of the medium should also approximately correspond to biological tissue, in order for the thermal dissipation that occurs to approximate the real conditions. In the case of implants that are implanted so as to remain in the tissue and also in air (in part), the medium should accordingly have the electromagnetic properties of air and/or approximate said properties. The medium may, as mentioned, be air.

In the method according to the invention, it is not essential to carry out measurements on a real phantom comprising a real implant located therein. The heating of the implant and/or of the medium surrounding said implant can also be detected by means of a numerical simulation of the propagation of the electromagnetic radiation in the test volume and the absorption of the electromagnetic radiation in the implant. Algorithms for the numerical simulation of electromagnetic field distributions generated by specific antenna arrangements are known from the prior art. Simulation methods of this kind can be used without problem according to the invention. Reference should also be made for example to the article by Z. Chen et al. in IEEE Transactions on Microwave Theory and Techniques, Vol. 64, No. 3, pages 972-981.

BRIEF DESCRIPTION OF THE SEVERAL VIEWS OF THE DRAWINGS

Embodiments of the invention will be explained in greater detail in the following, with reference to the drawing. In the drawing:

FIG. 1: is a schematic view of a device according to the invention for testing the MR-safety of an implant.

DESCRIPTION OF SPECIFIC EMBODIMENTS OF THE INVENTION

A device according to the invention is shown schematically in FIG. 1. Said device comprises a phantom 1 in the form of a cuboid container that forms a test volume within the meaning of the invention. The dimensions of the container are for example 600×600×2400 mm. The test volume is filled with a medium 2, the electric permittivity and electrical conductivity of which approximates that of biological tissue (e.g. $\varepsilon_r=78$ and $\sigma=0.47$). The device shown furthermore comprises an RF transmitter which is denoted as a whole by reference sign 3. Said RF transmitter is used to emit radio-frequency electromagnetic radiation into the test volume of the phantom 1. In this case, the frequency of the electromagnetic radiation is in the range of typical MR frequencies, i.e. in the range between 5 Hz and a few 100 MHz. The test volume of the phantom 1 receives a medical implant 4 to be tested. In the embodiment shown, the implant is elongate, e.g. wire-like. However, any other implant can in principle also be tested using the device shown. Furthermore, an optical fiber thermometer or radiation thermometer 5 is provided as a means for detecting the heating of the implant 4 and/or of the medium 2 surrounding said implant, which thermometer measures the temperature at the surface of the implant 4. Other types of sensors, such as local temperature sensors arranged in the medium for example, can also be used, although said sensors may interfere with the electromagnetic field. The heating can also be determined indirectly, using sensors that detect the electric and/or magnetic field in the surroundings of the implant 4. In order to generate the desired field distribution, the RF transmitter 3 comprises an assembly of a plurality of antenna elements 6. These may be straight microstrips that extend so as to be mutually parallel. Antenna elements of other designs can also be used. The antenna elements 6 are applied directly to the surface of the container that forms the phantom 1. In the embodiment, the antenna elements 6 are applied to just one of the total of six walls of the container. The antenna elements 6 which are formed as microstrips in this case, extend transversely to the longitudinal extension of the test volume. Coupling the radiation into the test volume from just one side is sufficient for generating different field distributions, according to the invention, in the near field of the antenna elements 6, for testing the MR-safety. Each antenna element 6 can be supplied, by means of the RF transmitter 3 shown, with an RF signal having an amplitude and phase that can be individually specified for said antenna element 6. Four antenna elements 6 are provided in the embodiment shown. Each of the antenna elements 6 is connected to the output of an RF transmitter amplifier 7. An adjustable phase shifter 8 and an adjustable attenuator 9 are connected upstream of each RF transmitter amplifier 7. At the inputs thereof, the attenuators 9 are connected to an RF synthesizer 10 which generates a phase-stable RF signal, of the desired frequency, at each output.

However, the invention does not essentially require real measurements to be made on a real phantom comprising a real implant located therein. The heating of the implant and/or of the medium surrounding said implant can also be detected by means of a numerical simulation of the propagation of the electromagnetic radiation in the test volume and the absorption of the electromagnetic radiation in the implant. Known methods for the numerical simulation of the electromagnetic field distribution can be used for this purpose in the arrangement shown in FIG. 1. The deposition of the RF power owing to the presence of the implant 4 is to be calculated as follows:

$$p = \int^V (p_{implant}(v) - p_{empty}(v)) \cdot dV,$$

Wherein $p_{implant}(V)$ is the RF dissipation power density in the presence of the implant, and $p_{empty}(v)$ is the RF dissipation power density without the implant. V is the relevant volume (also referred to as the "hotspot integration volume" or HSIV). The HSIV is defined as a coherent volume, in which $p_{implant}(v)$ is significantly greater than $p_{empty}(v)$.

Approximately the tangential electrical field $E_{tan}(z)$ that is generated along the trajectory (longitudinal extension) of the implant 4 when no implant 4 is located in the phantom 1 is used as a measure for the RF field. The position along the trajectory of the implant 4 of the overall length L (e.g. wire length) is denoted z. The calculation of the RF dissipation power density owing to the implant 4, according to $E_{tan}(z)$, can be based on a model of the implant 4 that provides a calibration factor A and a transfer function S(z) that are to be determined (optionally empirically) for the relevant implant. The power deposition by the implant can then be calculated in a simple manner as:

$$p = A \cdot |\int_0^L S(z) \cdot E_{tan}(z) \cdot dz|^2$$

In this manner, the in vivo RF power deposition is calculated for different field distributions $E_{tan}(z)$ generated by the antenna assembly. The RF dissipation power density obtained can then be converted into a temperature change, i.e. local heating at the location of the implant 4. The implant 4 is to be assessed as safe if the temperature increase is below a specified threshold value.

What is claimed is:

1. Device for testing the MR-safety of an implant (4) comprising a phantom (1) that has a test volume filled with a medium (2), wherein the test volume receives the implant (4) to be tested, at least one RF transmitter (3) that emits radio-frequency electromagnetic radiation into the test volume, and comprising means (5) for detecting the heating of the implant (4) and/or of the medium (2) surrounding said implant;
wherein the RF transmitter (3) comprises an assembly of a plurality of antenna elements (6), wherein each antenna element (6) can be supplied with an RF signal having an amplitude and/or phase that can be individually specified for said antenna element (6);
wherein the antenna elements (6) are connected to a multi-channel RF transmitter amplifier, wherein the amplitude and/or phase can be individually adjusted in each channel.

2. Device according to claim 1, wherein the RF transmitter (3) comprises an assembly of a plurality of antenna elements (6), wherein each antenna element (6) can be supplied with an RF signal having an amplitude and/or phase that can be individually specified for said antenna element (6).

3. Device according to claim 1, wherein the antenna elements (6) are applied to the surface of the test volume, or to a wall that defines the test volume.

4. Device according to claim 1, wherein test volume has a cuboid geometry, wherein the antenna elements (6) formed as microstrips extend substantially transversely to the longitudinal extension of the cuboid.

5. Device according to claim 1, wherein the medium corresponds to biological tissue in terms of electric permittivity and electrical conductivity.

6. Device according to claim 1, wherein the medium is a liquid or a gel or air.

7. Device for testing the MR-safety of an implant (4), comprising a phantom (I) that has a test volume filled with a medium (2), wherein the test volume receives the implant (4) to be tested, at least one RF transmitter (3) that emits radio-frequency electromagnetic radiation into the test volume, and comprising means (5) for detecting the heating of the implant (4) and/or of the medium (2) surrounding said implant;
wherein the RF transmitter (3) comprises an assembly of a plurality of antenna elements (6), wherein each antenna element (6) can be supplied with an RF signal having an amplitude and/or phase that can be individually specified for said antenna element (6);
wherein the antenna elements (6) are microstrips which extend in parallel with at least one surface of the test volume.

8. Device according to claim 7, wherein the antenna elements (6) are mutually parallel, straight microstrips.

9. Method for testing the MR-safety of an implant (4), wherein a test volume that is filled with a medium (2) receives the implant (4) to be tested and is subjected to radio-frequency electromagnetic radiation by at least one RE transmitter (3), wherein the heating of the implant (4) and/or of the medium (2) surrounding said implant is detected;
wherein the electromagnetic radiation is applied in such a way that the direction of the electrical field extends so as to be substantially in parallel with the implant surface.

10. Method according to claim 9, wherein the RF transmitter (3) comprises an assembly of a plurality of antenna elements (6), wherein each antenna element (6) can be supplied with an RF signal having an amplitude and/or phase that can be individually specified for said antenna element (6), such that an electromagnetic field is generated at the location of the implant (4) that corresponds to the electromagnetic field that is generated in the body of a patient during an MR examination.

11. Method according to claim 9, wherein the implant is wire-like.

12. Method according to claim 9, wherein the heating of the implant (4) and/or of the medium surrounding said implant is detected by a numerical simulation of the propagation of the electromagnetic radiation in the test volume and by calculating the absorption of the electromagnetic radiation in or at the implant.

* * * * *